(12) United States Patent
Ciufolini et al.

(10) Patent No.: US 6,218,540 B1
(45) Date of Patent: Apr. 17, 2001

(54) PROCESS FOR PREPARING CAMPTOTHECIN

(75) Inventors: Marco Ciufolini, Villeurbanne Cedex (FR); Frank Roschangar, Durham, NC (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 09/230,683

(22) PCT Filed: Jul. 30, 1997

(86) PCT No.: PCT/US97/14355

§ 371 Date: May 4, 1999

§ 102(e) Date: May 4, 1999

(87) PCT Pub. No.: WO98/04557

PCT Pub. Date: Feb. 5, 1998

Related U.S. Application Data

(60) Provisional application No. 60/022,401, filed on Jul. 30, 1996.

(51) Int. Cl.$^7$ .................. C07D 491/22; C07D 471/22; C07D 215/18

(52) U.S. Cl. ............................ 546/23; 546/48

(58) Field of Search ........................ 546/23, 48

(56) References Cited

FOREIGN PATENT DOCUMENTS

WO 92/11263 * 7/1992 (WO) .

* cited by examiner

*Primary Examiner*—Bruck Kifle
(74) *Attorney, Agent, or Firm*—Thomas J. Dodd

(57) ABSTRACT

A process for preparing the anti-cancer drug camptothecin (CPT) and certain derivatives thereof. The process includes the reacting of three base reagents and a five-step process for synthesizing optically pure CPT in high overall yield from inexpensive starting materials.

1 Claim, No Drawings

PROCESS FOR PREPARING CAMPTOTHECIN

CROSS-REFERENCE TO RELATED APPLICATIONS

This application is derived from United States Provisional Patent Application, Ser. No. 60/022,40 filed Jul. 30, 1996, and priority of that application is hereby claimed under 35 USC 119(e).

BACKGROUND OF THE INVENTION (20S)-(+)-Camptothecin, a pyrrolo [3,4-b] quinoline alkaloid, is the active principle of the Chinese tree, Camptotheca acuminata Decne, extracts of which have been used for centuries in traditional Chinese medicine to treat cancer. The alkaloid is mostly found in the bark of the plant, a fast growing deciduous tree native only to China and Tibet, where it is known as xi shu ("happy tree").

Camptotheca belongs to the family Nyssaceae (tupelo family) and may reach a height of about 25 m. It was first introduced to the United States in 1911 as an ornamental plant and on several occasions subsequently. More recently, C. acuminata plantations were established in southern Louisiana in an effort to provide raw plant materials for the production of camptothecin. The alkaloid may also be obtained from trees of the species Nothapodytes, which are native to the Indian subcontinent.

1.1 Scientific Interest in CPT

CPT was first isolated by Wall et al. in 1966 during an antitumor screening program, and immediately it generated a great deal of interest, both in the clinical and the chemical arenas, as a new agent for the treatment of human malignancy. The compound itself is highly insoluble in aqueous media, but the sodium salt, obtained by alkaline hydrolysis of the lactone ring, displayed good water solubiliy and was easily formulated for intravenous administration. As a consequence, phase I clinical trials were launched in the early 1970's in patients with an advanced form of gastrointestinal cancer. In retrospect, those protocols were poorly designed (vide infra), but in any event they led to the erroneous conclusion that CPT was only marginally effective. The drug did produce partial remissions in some patients, but the trials were eventually halted because of severe toxic side effects.

1.2 Mechanism of Action: Inhibition of Topoisomerase I

Details of the mechanism of action of CPT remained a mystery until 1985, when Liu et al. discovered that the substance is a specific inhibitor of topoisomerase I (Topo I), an essential enzyme for DNA replication and transcription. Topo I is a monomeric protein with a MW of ca.100 kD that relaxes (i.e., unwinds) torsionally strained (supercoiled) DNA ahead of active transcription and translation sites. The enzyme initially binds noncovalently to double-stranded DNA, but then it creates a transient break in one strand and concomitantly becomes covalently bound to the 3'-phosphoryl end of the nicked nucleic acid strand. The unbroken DNA strand is allowed to unwind once and to pass through the break site, before topo I religates the cleaved DNA and reestablishes the double-stranded configuration These events constitute an obligatory stage of DNA replication and transcription, as the chromosomes must be unwound in order for the cell to express genetic information or to divide. The covalent complex between topo I and a single DNA strand, also termed the "cleavable complex", is in rapid kinetic equilibrium with the noncovalently bound complex (the "noncleaveable complex"). Camptothecin is believed to express its activity by reversibly binding to the cleavable complex and stabilizing it, thereby inhibiting religation of the nicked DNA strand. As a consequence, the advancing DNA polymerase operating in the replicating fork soon "collides" with the stabilized cleavable complex and creates an irreparable double-strand break, which is fatal to the cell.

Cancer cells are more vulnerable to topoisomerase inhibition than normal cells, because they grow and reproduce at a much faster rate. Even more significantly, elevated concentrations of topo I have been found in many different tumor cells. In 1994, CPT was also found to inhibit both acute and chronic HIV-I infections. These observations have stimulated renewed interest in camptothecin, and as a result, much research in its pharmacology, medicinal chemistry and total synthesis is currently underway. Camptothecin itself has been used in China to treat leukemias and carcinomas of the stomach and liver, but it is not is not approved by FDA for use in the US. Considerably more promising are a number of semisynthetic derivatives currently being tested in phase I and phase II clinical trials. Examples include Gl 147211C, irinotecan (CPT-11), 9-aminocamptothecin (9-AC), 9-amino-10,11-methylenedioxy camptothecin (9-AC-10,11-MD) and topotecan. The latter substance was approved by FDA in May 1996. Positive results have recently been reported in the treatment of diverse neoplasms, such as colon and breast cancers, malignant melanoma, small-cell lung cancer, ovary, leukemia and non-Hodgkin's lymphoma. Toxicity remnains a problem, major side effects including severe diarrhea, nausea, leukopenia, and possibly bone marrow depression.

1.3 Relationship Between CPT Structure and Activity

The relationship between the structure of CPT and in vitro and in vivo activity has been reported in detail, hence this section will summarize only major findings.

1. An intact E ring (lactone moiety) is necessary for activity.
2. The (20S) configuration is an absolute requirement, (20R)-CPT or analogs being inactive in vitro and in vivo.
3. With the exception of SN-38, only ring A derivatives increase antitumor activity. Substitutions at C-9 or C-10 generally enhance activity.
4. The pentacyclic structure of CPT is an absolute requirement. Tetracyclic analogs or bicyclic and tricyclic analogs are inactive.
5. Disubstitution in general leads to CPT analogs with reduced or no activity, the exception being the 10,11-methylenedioxy moiety, which greatly increases activity. Substitution in the 11- and 12-positions gave CPT analogs which exhibited reduced activity or total inactivation.
6. The a-hydroxy lactone moiety in ring E is required.
7. Substitution of nitrogen for OH or lactone oxygen in ring E leads to inactivation.
8. The pyridone ring D is required. Replacement of the pyridone ring by an aromatic ring results in inactivation.
9. The C-20 ethyl substituent is required, although there is some flexibility; for example, substitution of a 20-allyl group resulted in good activity, whereas substitution of a methyl group led to inactivation.

1.4 Biosynthetic Pathway

In 1967 Wenkert et al. hypothesized that CPT is derived biosynthetically from tryptophan and secologanine. Winterfeld later expanded on this idea based on his own finding that indole derivatives underwent facile auto-oxidation to quinolones in vitro.

The proposed biosynthetic pathway of CPT was later verified and further elaborated by Hutchinson via plant feeding experiments with regiospecifically labeled precursors. It seems clear that strictosamide is a key precursor. Transformation of strictosamide into CPT is considered to be possible through ring BC oxidation followed by recyclization, ring D oxidation, removal of the C-21 glucose moiety and ring E oxidation.

1.5 Previous Syntheses

Further clinical evaluation of CPT, and congeners is intimately dependent on the availability of an efficient total synthesis. The natural product is exceedingly rare and costly. It may be obtained virtually exclusively from the People's Republic of China through unreliable suppliers authorized by the Chinese Government. Large orders (100 g) are priced at ca. $ 35–40/g. The latest (1996–97) catalog from the Aldrich Chemical Co. lists CPT for $ 127.50/g: nine times the current price of pure gold ($ 395/oz=$ 14.10/g). In recent times it has become apparent that certain derivatives of CPT possess more desirable pharmacological properties. The preparation of these substances by semisynthesis is often lengthy and inefficient, because the natural product does not lend itself readily to derivatization, and because its insolubility in most organic solvents creates a host of technical problems. In this light, total synthesis appears to be an entirely acceptable alternative, if not a much better approach. Yet the deceptively simple structure of camptothecin is endowed with robust defenses against a synthetic attack, not the least of which is the crucial configuration of the C-20 center. Despite the fact that twenty-five years have elapsed since the first total synthesis of CPT was accomplished, practical avenues have emerged only beginning in 1994. It would be inappropriate to discuss all the numerous published syntheses of CPT in detail, since comprehensive reviews are available. We shall survey instead only the most significant efforts, with the focus on recent enantioselective routes.

The first total synthesis of (±)-CPT was reported by Stork and Schultz in 1971. A key transformation was a base-catalyzed Friedländer condensation of pyrrolidinone with 2-aminobenzaldehyde to give the tricyclic pyrrolo [3,4-b] quinoline acid. This was converted to the tetracyclic b-ketolactam, which was advanced to (±)-CPT. Racemic CPT was thus prepared in 17 steps and in ca. 1–2% overall yield.

Danishefsky recently improved his 1971 synthesis of (±)-CPT, the second one ever to be published, to 9 steps and 31% yield starting from vinylogous urethane, through intermediacy of the key tricyclic lactone. A key strategic idea is the formation of the lactone by hydroxymethylation of the pyridone derived from, a transformation that is poorly regioselective unless one of the reactive sites of that heterocycle is blocked. This function is delegated to a carbomethoxy group occupying a position corresponding to C-14 of CPT. That functionality also increases the acidity of protons on the vinylogous CH2 group (C-2 in CPT), thereby facilitating the subsequent introduction of a ketone required for Friedlander reaction.

Winterfeldt discovered in 1971 that indoles are autoxidized to quinolones in strongly basic dimethylformamide solution. The ease with which this transformation occurred led to the hypothesis that quinolones may be biosynthetic intermediates. Several of the proposed precursors were subsequently isolated from plant extracts.

An imaginative total synthesis of CPT was readily developed on the basis of this facile interconversion, which in the specific case evolved from triester. Racemic CPT was thus obtained in 13 steps and 12% yield from the known ester.

The first synthesis of (+)-camptothecin was announced in 1975 by Corey. A characteristically elegant synthetic design resting on the merger of chiral pseudoacid chloride with tricyclic amine was ultimately marred by poor yields (0.3% overall) and lengthy sequences (21 steps). Scalemic lactone was secured through resolution of the racemate via its diastereomeric quinine salts, followed by treatment with methyl chloroformate, and removal of the quinine salt by quaternization with methyl iodide.

Resolution was also a central feature in the Wall synthesis of (+)-CPT. Pyridone was prepared by condensation of 2-cyanoacetamide with the enol ether of ethyl acetpyruvate and advanced to in 12 steps and 14% yield. Resolution was conducted by cleavage of the lactone ring with (S)-(−)-a-methylbenzylamine, separation of the diastereomers, and relactonization. The loss of at least one-half was still a drawback.

The first attempt to produce a scalemic CPT intermediate by means other than resolution was reported by Tagawa. The cornerstone of this approach is a diastereoselective ethylation of the enolate. A chiral auxiliary derived from D-proline (expensive—$ 16/g from the Aldrich Chemical Co.) induced an 82:18 diastereoselectivity in favor of the desired stereoisomer, which was recrystallized to optical purity. Camptothecin was therefore reached in eight steps and 19% yield, which itself resulted from a multistep sequence as reported earlier by Wall. The overall yield was therefore around 7% over no less than 14 steps.

The best enantioselective synthesis of camptothecin known prior to our work was reported in 1994 by Fang and collaborators at the Glaxo Pharmaceutical Company. Their approach is conceptually similar to a route described by Comins, with whom the Glaxo group has had a long standing collaboration on the CPT problem, but it differs from the Comins plan in that asymmetry is created by a Sharpless dihydroxylation instead of a diastereoselective carbonyl addition. A common theme remains the Comins metallation technology for the elaboration of the central pyridone unit.

The Comins synthesis (3% overall yield for 8 steps) elaborated a "stripped down" pyridone to iodide, which was lithiated (n-BuLi) and treated with the 2-ketobutyrate ester of (−)-trans-2-(a-cumyl)-cyclohexanol to afford in 88% diastereomeric excess. A drawback of this approach is that the chiral auxiliary does not appear to be commercially available; nevertheless, it is recoverable and recyclable. The ring ABC triad was installed in an elegant sequence involving N-alkylation followed by radical cyclization.

The Fang strategy centers on asymmetric Sharpless dihydroxylation. The creation of this pyridine relies largely on Comins technology, with an intramolecular Heck reaction as an additional interesting twist. Rings ABC were introduced also as shown earlier by Comins, except that an intramolecular Heck reaction was preferred to a radical cyclization.

An even more recent enantioselective synthesis of CPT has been disclosed by Curran. No conceptual advances are evident in this work with respect to the issue of enantioselectivity; indeed, the key intermediate was prepared in a manner identical to Fang's. However, an elegant cascade of radical processes was utilized to complete rings B and C of the natural product. Highly enantiomerically enriched CPT (95% ee) thus emerged in 9 steps and 3% overall yield from pyridine.

SUMMARY OF THE INVENTION

This invention relates to a novel high overall yield process for preparing relatively pure camptothecin. The process includes the synthesis of several novel intermediates and the use of commercially available starting reagents to prepare relatively pure (20S)-(+)-camptothecin in a five step process with about a 51% overall yield.

DETAILED DESCRIPTION OF THE PREFFERED EMBODIMENTS

The preferred processes herein described are not intended to be exhaustive, nor are they intended to limit this invention to the details herein given. Instead, the processes are disclosed to enable one skilled in the art to practice the teaching of the invention.

(20S)-(+)-camptothecin (also referred to below as CPT) has the following formula:

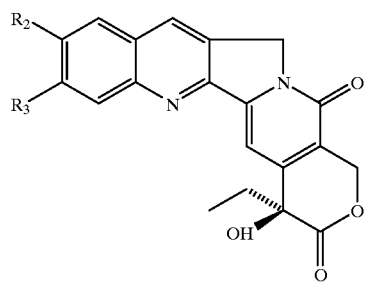
(I)

In CPT, $R_2$ and $R_3$ are hydrogen. Derivatives of CPT wherein $R_2$ and $R_3$ are individually hydroxy, or another known organic moiety, can be prepared using only slight variations of this process.

The lactone form of CPT (shown above as Formula I) is known to be the active, and therefore desired, form of the compound. According to the process of this invention, CPT is formed from the following intermediate compounds in a five-step process as shown in the schemes and the specific examples which follow:

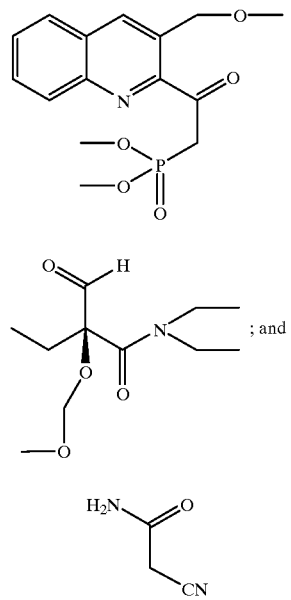

(IV)

(V)

; and (VI)

The overall process for synthesizing the lactone form of CPT is shown in Scheme 3, infra. Schemes 1 and 2 illustrate the synthesis of the key intermediates IV and V above, from commercially available starting reagents.

Scheme 1

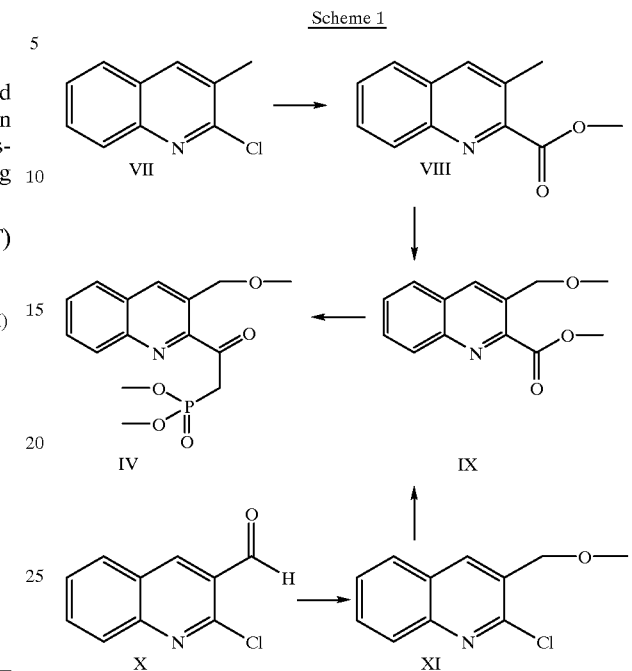

Scheme 1 illustrates the synthesis of the quinoline phosphonate ester intermediate IV which is used in the process of this invention. One of the primary objects of this invention is to provide for a novel synthetic high yield process for preparing camptothecin (in particular, the biologically active stereoisomer, 20S-(+)-CPT) which is also economical. Commercially available starting materials are preferred to minimize the costs of synthesis.

As shown in Scheme 1, the preferred starting reagent for preparing intermediate IV is a 2, 3 disubstituted quinoline derivative (substitutions at the 4, 5, 6 and 7 positions are also contemplated, should the final desired product be a CPT derivative). The most preferred derivatives of the starting reagents for Scheme 1 are those where the 2-moiety is a leaving group, such as a halogen atom or other easily removable group. The 3-moiety is preferably an alkyl group or similarly moiety which is easily removed, but which remains stable while reactions are performed on the 2-moiety. The most preferred 2- and 3-moieties are chloro and methyl, respectively.

The preferred first step in synthesizing intermediate IV is the esterification of the 2-moiety of 2-chloro-3-methylquinoline (VII) to an alkoxycarbonyl, preferably to 2-methoxycarbonyl moiety (intermediate VIII shown). This substitution may be achieved by using any of a variety of known carboxylation processes. The most preferred method shown utilizes cataylsts, such as sodium acetate and palladium II-diactetate. The most preferred first step utilizes $Pd(OAc)_2$ and NaOAc, and a phosphino alkyl compound (most preferred is bis-(diphenylphosphino) propane (dppp) which reacts with the diacetate palladium to form a Pd (IV) complex. The desired intermediate is formed in over 98% yield after filtering and washing steps.

Conversion of quinoline ester intermediate VIII to the 2-methoxymethyl quinoline ester intermediate IX is preferably performed in a two step process. First, the 3-methyl moiety is brominated by a common method, preferably by reacting intermediate VIII with a brominating reagent, such as N-bromosuccinimide, and a catalyst, under ultraviolet lighting. The 3-bromomethyl intermediate is then alkoxylated using methanol in an acidified solution to form the 3-methoxymethyl (MOM) intermediate IX. After extraction, washing and concentration, about a 55% yield of the desired intermediate IX is obtained.

Intermediate IX is then converted to the preferred quinoline phosphonate ester IV by a substitution reaction. Preferably, an in situ generated alkali phosphonate ester is generated from n-butyl lithium and a commercial phosphonate reagent, such as dimethyl methylphosphonate. The overall combined yield of the two steps is over 80%. Quinoline phosphonate ester IV is then set aside for later use in the overall process of preparing CPT.

As noted above, the quinoline phosphonate ester IV may include additional substitutions at any, some or all of the 4, 5, 6 and 7 positions (of the original starting reagent) to produce known derivatives of CPT(1). Additional chemistry performed to protect any 4, 5, 6 or 7 substituted moieties is within the purview of those skilled in the art.

Intermediate IV may also be prepared from aldehyde X by reducing the aldehyde to its MOM derivative XI, then substituting the methoxycarbonyl group at the two position to form intermediate IX.

Scheme 2

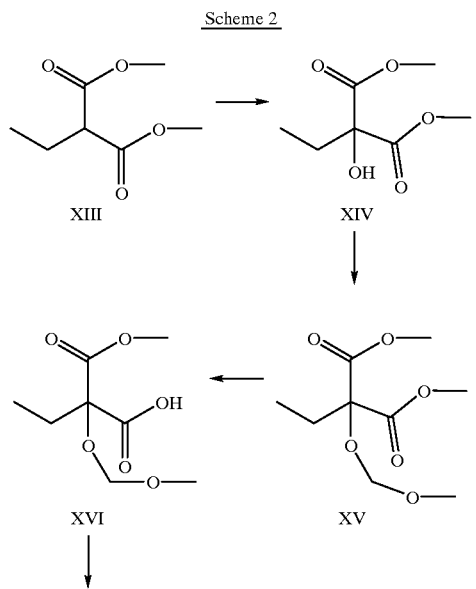

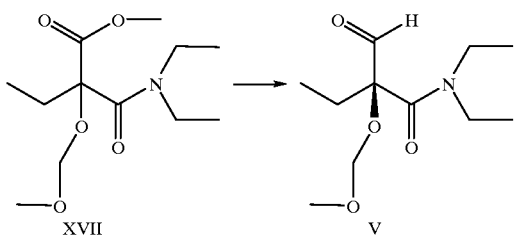

Scheme 2 illustrates the preparation of the preferred aldehyde intermediate V. This intermediate synthesis is stereoselective and provides the intermediate V which will produce the biologically active form of CPT(I), 20S-(+)-CPT.

The starting reagent for the preferred synthesis is the dimethyl ester of ethyl malonic acid XIII. Ozonolysis of this compound yields the hydroxy malonate intermediate XIV in over 70% yield.

The hydroxy moiety of malonate ester intermediate XIV is converted into a methoxymethyl moiety by reacting with a methoxymethylating agent, such as a methoxymethyl halide, most preferably methoxymethyl chloride in a basic solution to provide a near 100% quantitative yield of intermediate XV.

Next enantioselectivity of the ether and ethyl moieties and protonation is achieved by reacting intermediate XV with an enantioselective enzyme to form the carboxylic acid intermediate XVI. Preferred is an esterase enzyme, most preferably pig liver esterase, which protonates the 2 carboxylic acid and also effects optical rotation of the ethyl and MOM moieties into the desired (biologically active) configuration shown. This step produces about a 90% overall yield (over 98% e.e.) of the enantiomer shown.

Intermediate XVI is then converted to form the amide intermediate XVII. Specifically, the N,N-dialkyl carbonyl intermediate is formed by adding secondary and tertiary amines (most preferably, diethylamine and triethylamine) in the presence of a condensing agent (preferably a quaternary salt, such as 2-chloro-N-methylpyridinium iodide). Washing and drying the resulting compound provides a yield of about 90% of intermediate XVII.

Intermediate XVII is then reduced to aldehyde V by a common reducing agent, preferably an organo-substituted metal hydride, most preferably diisobutyl aluminum hydride (DIBAL). The reduction takes place at significantly lowered temperatures. After extraction, a near 100% yield of pure aldehyde V was obtained for carrying forward to Scheme 3.

Scheme 3

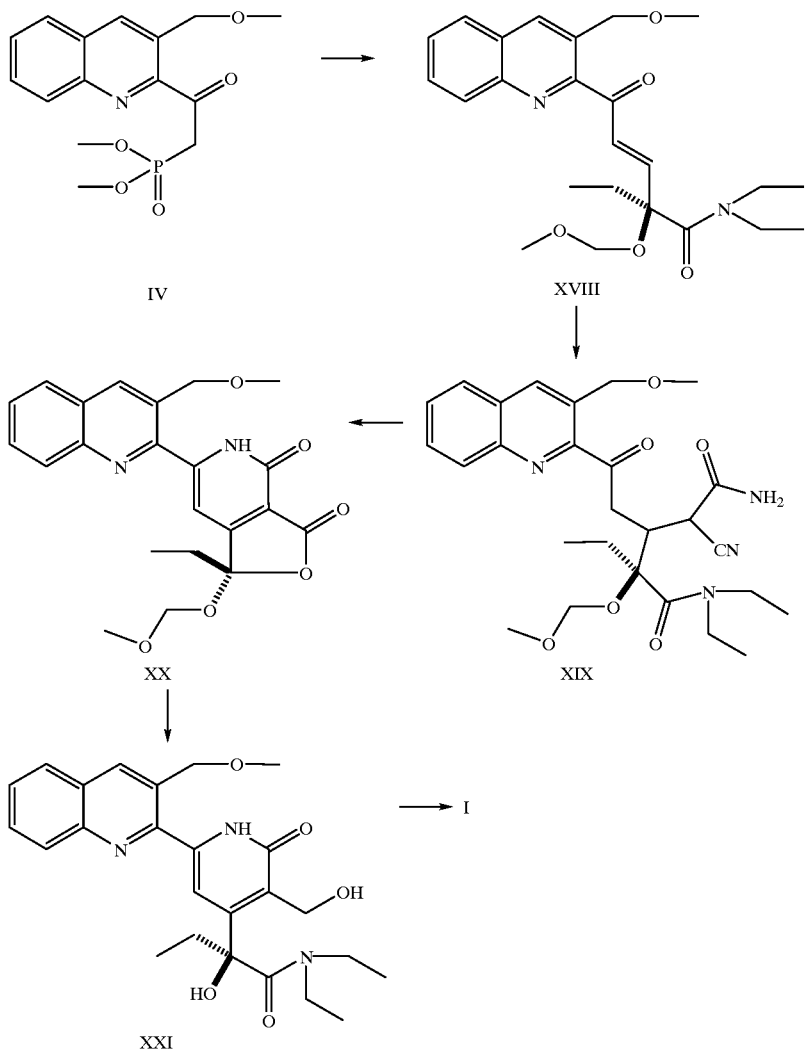

Scheme 3 illustrates the overall synthetic procedure for preparing 20S-(+)-CPT(I). In the first step of the synthesis shown, quinoline phosphonate ester intermediate IV is reacted with aldehyde V to form the enone intermediate XVIII. The reaction is carried out in the presence of one or more basic agents such as an alkoxide salt. Most preferred is potassium tert-butoxide. After the washing, drying and extraction procedures about an 80% quantitative yield of intermediate XVIII was produced.

Intermediate XVIII is then reacted with 2-cyanoacetamide V to form the saturated cyanoacetamide step intermediate XIX. Basic agents such as described in the above step are again utilized with the most preferred being potassium t-butoxide. Intermediate XIX is washed and concentrated to produce a near 100% quantitative yield.

Intermediate XIX is then reacted with one or more oxidizing agents, in conjunction with a strong acid and hydrolyzing agents, to form the pyridone ring and the lactone intermediate XX. Cyclization of the butyral lactone ring occurs during this step in which acetic and sulfuric acids are used along with oxidents, such as selenium dioxide, and tert-butyl hydroperoxide. After washing and concentrating, about 68% quantitative yield of intermediate XX is obtained.

Lactone intermediate XX is then reduced to the diol intermediate XXI. Excess quantities of a reducing agent such as the preferred sodium borohydride and cerium III chloride are employed to drive the reaction to completion. Heating, concentration and extraction is performed to yield intermediate XXI which is carried forward to the final step of the process without purification.

The final step of the process involves the cyclization of intermediate XXI to camptothecin I. The intermediate XXI is dissolved in a strong acid, most preferably a mineral acid such as sulfuric acid, and ethanol, then heated, extracted, dried and concentrated. Chromatography confirmed the conversion to camptothecin I in 94% quantitative yield from lactone intermediate XX.

As stated above, various substituted derivatives of CPT can be produced by altering the starting materials and employing well known protection/deprotection schemes to control the configuration and molecular make-up of the desired derivatives.

The following specific examples of the process are not intended to be exhaustive of the inventive process, but are disclosed to enable those skilled in the art to follow its teachings.

Experimental Protocols

Melting points (uncorrected) were measured on a Fischer-Johns hot stage apparatus. NMR spectra (ppm on the d scale) were recorded at room temperature on a Bruker AC 250 (250 MHz for 1H and 62.5 MHz for 13C) spectrometer from CDCl3 solutions, unless otherwise indicated. Splitting patterns are described as "s" (singlet), "d", "dd", "ddd", etc. (doublet, doublet of doublets, doublet of doublets of doublets), "t" (triplet), "q" (quartet), "m" (multiplet), and further characterized as "app" (apparent), "br" (br), or "c" (complex). IR spectra (cm-1) were obtained with a Perkin Elmer 1600 FTIR spectrophotometer from films deposited on NaCl plates. Low resolution mass spectra (m/e, solid probe, 70 eV EI) were obtained on a Finnigan 6000 quadrupole instrument. High resolution mass spectra (m/e, solid probe, 70 eV EI) were obtained on a Finnigan-MAT 4000 instrument. Analytical and preparative TLC was carried out with Merck silica gel 60 plates with fluorescent indicator. Spots were visualized with UV light or stained with iodine, molybdic acid (Solution of 24 g (NH4) 6Mo7O24 and 0.5 g Ce(SO4)2 in 500 ml of 10% aq. H2SO4) anisaldehyde, or Dragendorff reagents (Gordon, A. J., Ford, R. A. The Chemist's Companion; John Wiley & Sons, New York, N.Y., 1972; p. 378). Chromatographic silica gel was purchased from Jenssen (60–200 mesh) or Merck (230–400) mesh. THF was distilled from sodium benzophenone ketyl; dichloromethane was first passed through alumina, then distilled from CaH2; ethyl acetate was distilled at atmospheric pressure; methanol was dried over 4 Å molecular sieves. All other reagents and solvents were used as received.

EXAMPLES 1–13

Example 1

Ozonized oxygen was passed through ethyl dimethylmalonate, XIII (5.470 g, 20.5 mmol) adsorbed onto silica gel (66 g) at room temperature for 2 h. The mixture was transferred to a chromatographic column. Elution with 10% ethyl acetate/hexanes gave 1.094 g (20%) unreacted starting material and 4.321 g (71%) of hydroxymalonate XIV as a colorless oil.

$^1$H (CDCl$_3$): 3.81 (s, 6H), 3.73 (s, 1H), 2.12–2.03 (q, 2H, J=7.4 Hz), 0.94–0.88 (t, 3H, J=7.4 Hz) ppm; $^{13}$C (CDCl$_3$): 171.0, 79.4, 53.3, 28.1, 7.4 ppm; IR (film): 1691 cm$^{-1}$.

Example 2

Chloromethyl Methyl Ether (11.9 ml, 157 mmol) was added at room temperature to a solution of alcohol XIV (9.153 g, 52.0 mmol) and diisopropylethylamine (46 ml, 265 mmol) in CH$_2$Cl$_2$ (36 ml), and the mixture was then stirred at room temperature for 3 days. The reaction mixture was added to saturated aqueous NaHCO$_3$ and extracted with ethyl acetate. The combined extracts were washed with H$_2$O and with saturated aqueous NaCl solution, dried (Na$_2$SO$_4$) and concentrated. Purification by column chromatography (10% ethyl acetate/hexanes) gave 11.435 g (100%) of XV as a pale yellow oil.

$^1$H (CDCl$_3$): 4.86 (s, 2H), 3.77 (s, 6H), 3.36 (s, 3H), 2.17–2.08 (q, 2H, J=7.5 Hz), 0.91–0.85 (t, 3H, J=7.4 Hz) ppm; $^{13}$C (CDCl$_3$): 169.5, 93.2, 56.2, 52.7, 27.0, 7.4 ppm; IR (film): 1696 cm$^{-1}$; MS (CI+): m/z 221 (MH+), 189 (100%); HRMS (CI+): Calc. for C$_9$H$_{17}$O$_6$: 221.1025 (MH$^+$); Found: 221.1025 (MH$^+$).

Example 3

Malonate XV (1.380 g, 6.27 mmol) was suspended in 42 ml 25% DMSO-H$_2$O, the temperature was regulated to 35° C., and the pH was adjusted to 7.0 with 1 N NaOH. Pig Liver Esterase (1568 units) was added and the pH was maintained between 6.9 and 7.4 by addition of 1 N NaOH. When one equivalent of base had been added (3.5 hours), the reaction came to a halt (no further pH drop) and the system had become homogeneous. The mixture was basified to pH 8 and washed with ether, then acidified to pH 2, saturated with solid NaCl, and extracted with ethyl acetate. The extracts were dried (Na$_2$SO$_4$), and concentrated. Kugelrohr removal of DMSO at 45° C. provided 1.168 g (90%) of pure XVI as a colorless oil.

$[a]_D$: +10.00 (c 6.150, CHCl$_3$); $^1$H (CDCl$_3$): 8.81 (broad, 1H), 4.84 (s, 2H), 3.75 (s, 3H), 3.36 (s, 3H), 2.17–2.07 (dq, 2H, J$_1$=7.4 Hz, J$_2$=2.9 Hz), 0.91–0.85 (t, 3H, J=7.5 Hz) ppm; $^{13}$C (CDCl$_3$); 172.3, 169.3, 93.1, 82.9, 56.3, 52.8, 26.6, 7.2. ppm; IR (film): 1691 cm$^{-1}$; MS (CI+): m/z 207 (MH$^+$), 175 (100%); HRMS (CI+): Calc. for C$_8$H$_{15}$O$_6$: 207.0869 (MH$^+$); Found: 207.0870 (MH$^+$).

Example 4

Diethylamine (3.1 ml, 29.9 mmol) and triethylamine (7.3 ml, 52.4 mmol) were added to a solution of acid XVI (3.069 g, 14.9 mmol) in CH2Cl2 (150 ml), and the solution was cooled to 0° C. After careful addition of 2-chloro-N-methylpyridinium iodide (6.3 g, 23.9 mol), the mixture was allowed to warm to room temperature over 20 minutes. Upon completion of the reaction (NMR), the mixture was added to saturated aqueous NaHCO3 and extracted with ethyl acetate. The extracts were washed with H2O and with saturated aqueous NaCl solution, dried (Na2SO4) and concentrated. Chromatography (10% ethyl acetate/hexanes) gave 3.500 g (90%) of desired XVII as a pale yellow oil.

$[a]_D$: -67.4° (c 6.850, CHCl$_3$) $^1$H (CDCl$_3$): 4.69 (s, 3H), 3.76 (s, 3H), 3.72–3.10 (m, 4H), 3.41 (s, 3H), 2.36–2.06 (m, 2H), 1.12–1.06 (t, 3H, J=7.1 Hz), 1.07–1.02 (t, 3H, J=7.1 Hz), 0.87–0.81 (t, 3H, J=7.5 Hz) ppm; $^{13}$C (CDCl$_3$): 170.5, 166.4, 92.7, 84.9, 56.8, 52.3, 40.6, 40.4, 27.1, 13.1, 11.9, 7.4 ppm; IR (film): 1711, 1650 cm$^{-1}$; MS (CI+): m/z 262 (MH$^+$), 230 (100%); HRMS (CI+): Calc. for C$_{12}$H$_{24}$NO$_5$: 262.1654 (MH$^+$); Found: 262.1654 (MH$^+$); EA:(Calc.) C: 55.48 (55.17); H: 8.88 (8.81); N: 5.29 (5.36).

Example 5

Diisobutylaluminum hydride (1.5 M solution in toluene, 13.9 ml, 20.9 mmol) was added at a slow dropwise rate into a cold (–78° C.) solution of ester XVII (2.018 g, 7.73 mmol) in toluene (19 ml). The mixture was stirred at –78° C. for 2 hours after completion of addition, then treated with cold MeOH (–78° C., 3.5 ml) and poured into cold saturated aqueous NaHCO$_3$ (0° C.), with vigorous swirling over 15 minutes. The resulting slurry was extracted with ethyl acetate. The extracts were washed with saturated aqueous NaCl, dried (Na$_2$SO$_4$) and concentrated to give 1.792 g of essentially pure V (100%), pale yellow oil, which was best used in crude form.

$[a]_D$: -49.5° (c 6.600, CHCl$_3$); $^1$H (CDCl$_3$): 9.58 (s, 1H), 4.68–4.61 (AB, 2H, J=6.9 Hz), 3.56–3.04 (m, 4H), 3.30 (s, 3H), 2.21–2.09 (m, 1H), 1.91–1.79 (m, 1H), 1.09–1.01 (dt, 6H, J=6.9 Hz), 0.82–0.76 (t, 3H, J=7.6 Hz) ppm; $^{13}$C (CDCl$_3$): 196.1, 167.2, 92.7, 86.7, 56.1, 40.5, 40.1, 24.6, 13.5, 12.1, 7.6 ppm; IR (film): 1785, 1646–1619 (broad) cm$^{-1}$; MS (CI+): m/z 232 (MH$^+$), 200 (100%); HRMS (CI+): Calc. for C$_{11}$H$_{22}$NO$_4$: 232.1549 (MH$^+$); Found: 232.1539(MH$^+$); EA:(Calc.) C: 57.50 (57.14); H: 9.25 (9.09); N: 5.88 (6.06).

Example 6

A high pressure reactor was charged with a stirring bar, 2-chloro-3-methylquinoline VII (4.042 g, 22.8 mmol), Pd(OAc)$_2$ (51 mg, 0.23 mmol), 1,3-bis-(diphenylphospino) propane (188 mg, 0.46 mmol), NaOAc (1.867 g, 22.8 mmol), MeOH (2.3 ml) and DMF (7.6 ml), and pressurized to 105 atm of CO. The mixture was stirred for 2 days at 140° C., then cooled, diluted with ether, filtered through celite, washed with H$_2$O and saturated aqueous NACl, dried (Na$_2$SO$_4$) and concentrated to afford 4.484 g (98%) of pure VIII as a yellow oil.

$^1$H (CDCl$_3$): 8.20–8.16 (d, 1H), 8.03 (s, 1H), 7.79–7.75 (dd, 1H, J$_1$=8.1 Hz, J$_2$=1.0 Hz), 7.73–7.66 (dt, 1H, J$_1$=6.9 Hz, J$_2$=1.5 Hz), 7.61–7.55 (dt, 3H, J$_1$=7.1 Hz, J$_2$=1.2 Hz), 4.05 (s, 3H), 2.69 (s, 3H) ppm; $^{13}$C (CDCl$_3$): 166.8, 149.2, 145.8, 138.1, 130.4, 129.9, 129.3, 129.0, 128.3, 126.7, 52.8, 19.8 ppm; IR (film): 1678 cm$^{-1}$; MS (EI+): m/z 201 (MH$^+$), 143 (100%); HRMS (EI+): Calc. for C$_{12}$H$_{11}$NO$_2$: 201.0789 (MH$^+$); Found: 201.0785 (MH$^+$).

Example 7

A solution of methylquinoline VIII (4.253 g, 21.2 mmol), N-bromossuccinimide (3.390 g, 19.0 mmol) and benzoyl peroxide (26 mg, 0.11 mmol) in carbon tetrachloride (42 ml) was irradiated with two 275W sunlamps for three hours. The solution was filtered through cotton and concentrated. The crude mixture of desired product, unreacted starting material, and dibrominated compound was used in the next step without further purification. The data were obtained from purified material.

M.p.: 89–90° C.; $^1$H (CDCl$_3$): 8.29(s, 1H), 8.26–8.22 (d, 1H, J=8.3 Hz), 7.88–7.83 (dd, 1H, J$_1$=9.0 Hz, J$_2$=1.6 Hz), 7.82–7.76 (dt, 1H, J$_1$=6.9 Hz, J$_2$=0.9 Hz), 7.69–7.63 (dt, 1H, J$_1$=8.1 Hz, J$_2$=1.1 Hz), 5.06 (s, 2H), 4.11 (s, 3H) ppm; $^{13}$C (CDCl$_3$): 165.9, 147.5, 146.3, 138.6, 130.4, 129.8, 128.8, 128.2, 127.2, 53.1, 30.0 ppm; IR (film): 1678 cm$^{-1}$; MS (EI+): m/z 279 & 281 (M$^+$), 200 (100%); HRMS (EI+): Calc. for C$_{12}$H$_{10}$$^{79}$BrNO$_2$: 278.9895 (M$^+$); Found: 278.9876 (M$^+$).

Example 8

A solution of the crude NBS product mixture in MeOH (100 ml) and H$_2$SO$_4$ (5 ml) was refluxed for two days, then cooled and poured into saturated aqueous NaHCO$_3$. The mixture was extracted with CHCl$_3$, and the extracts were washed with H$_2$O, saturated aqueous NaCL, then dried (NA$_2$SO$_4$) and concentrated. Chromatography (2.5% ethyl acetate/hexanes) followed by recrystallization with toluene/hexanes gave 2.696 g (55%) of desired IX as white crystals.

M.p.: 63–64° C.; $^1$H (CDCl$_3$): 8.43(d, 1H, J=0.7 Hz), 8.25–8.22 (d, 1H, J=8.4 Hz), 7.89–7.86 (dd,1H, J$_1$=8.1 Hz, J$_2$=0.9 Hz), 7.79–7.72 (dt, 1H,J$_1$=6.9 Hz, J$_2$=1.4 Hz), 7.67–7.60 (dt, 3H, J$_1$=7.0 Hz, J$_2$=1.2 Hz), 4.95 (d, 2H, J=1.0 Hz), 4.05 (s, 3H), 3.54 (s, 3H) ppm; $^{13}$C (CDCl$_3$): 166.0, 146.4, 145.7, 135.0, 131.5, 129.5, 128.3, 128.0, 127.1, 70.6, 58.4, 52.5 ppm; IR (film): 1723 cm$^{-1}$; MS (EI+): m/z 231 (M$^+$), 216, 184 (100%); HRMS (EI+): Calc. for C$_{13}$H$_{13}$NO$_3$: 231.0895 (M$^+$); Found: 201.0895 (M$^+$).

Example 9

A 2.5 M solution of n-butyllithium in hexanes was added dropwise to a cold (−78° C.) solution of 2–3 crystals of 1,10-phenanthroline in THF (4.5 ml), in a flame-dried flask. When the indicator changed color (2–3 drops), 5 more ml of BuLi solution was added (12.5 mmol), followed by slow addition of neat dimethyl methylphosphonate (1.4 ml, 12.9 mmol). The reaction mixture was stirred −78° C. for 30 minutes, then quinoline ester IX (1,369 g, 5.93 mmol) in THF (4 ml) was added. Stirring at −78° C. was continued for 2.5 hours, then the reaction was carefully quenched with 3.15 ml of 4 N HCl and warmed to room temperature. Extraction with ethyl acetate and concentration left a residue that was Kugelrohr-purified at 55° C. The thick yellow oil left in the distillation flask was microanalytically pure IV (1.910 g, 100%), and slowly solidified upon standing.

M.P.: 51° C.; $^1$H (CDCl$_3$): 8.52(d, 1H, J=0.8 Hz), 8.18–8.14 (dd, 1H, J$_1$=8.5 Hz, J$_2$=0.5 Hz), 7.91–7.88 (dd,1H, J$_1$=8.0 Hz, J$_2$=1.0 Hz), 7.80–7.73 (dt, 1H,J$_1$=8.5 Hz, J$_2$=1.5 Hz), 7.69–7.63 (dt, 1H, J$_1$=8.1 Hz, J$_2$=0.5 Hz), 4.99 (d, 2H, J=1.2 Hz), 4.28–4.19 (d, 2H, J=22.3 Hz), 3.79–3.74 (d, 6H, J=11.2 Hz), 3.58 (s, 3H) ppm; $^{13}$C (CDCl$_3$): 195.6, 195.5, 149.3, 145.6, 134.8, 132.7, 130.0, 129.9, 129.4, 129.1, 127.6, 71.2, 58.9, 53.0, 52.9, 46.3, 37.7, 35.6, ppm; IR (film): 1797 cm$^{-1}$; MS (EI+): m/z 323 (M$^+$), 308, 291, 182 (100%); HRMS (EI+): Calc. for C$_{15}$H$_{18}$NO$_5$P: 323.0923 (M$^+$); Found: 323.0919 (M$^+$); EA:(Calc) C: 55.43 (55.73); H: 5.91 (5.61); N: 4.11 (4.33); P 9.86 (9.58).

Example 10

Phosphonate IV (1.503 g, 4.65 mmol) in 1,2-dimethoxyethane (3.0 ml) was transferred into a cold (0° C.) solution of potassium tert-butoxide (603 mg, 5.12 mmol) in 1,2-dimethoxyethane (3.3 ml) in a flame-dried flask, and the resulting mixture was stirred at 0° C. for 30 minutes. The ice-bath was removed and aldehyde V (1.288 g, 5.58 mmol) in 1,2-dimethoxyethane (3.0 ml) was added. The reaction mixture heated to 50° C. for 12 hours, then cooled, poured into saturated aqueous NaHCO$_3$ and extracted with ether. The extracts were sequentially washed with saturated aqueous NaHCO$_3$, H$_2$O, and saturated aqueous NaCl, dried (Na$_2$SO$_4$) and concentrated. The residue was chromatographed with 10% ethyl acetate/hexanes to provide 1.588 g (80%) of enone XVIII as a yellow oil.

[a]$_D$: −56.1° (c4.720, CHCl$_3$); $^1$H (CDCl$_3$): 8.45(d, 1H, J=0.7 Hz), 8.16–8.13 (d, 1H, J$_1$=8.0 Hz), 7.89–7.86 (dd,1H, J$_1$=8.1 Hz, J$_2$=1.1 Hz), 7.78–7.72 (dt, 1H, J$_1$=6.8 Hz, J$_2$=1.5 Hz), 7.78–7.71 (d, 1H, J=16.1 Hz), 7.67–7.60 (dt, 1H, J1=6.9 Hz, J2=1.2 Hz), 7.12–7.06 (d, 1H, J=16.1 Hz), 4.98 (br. S, 2H), 4.77–4.69 (AB, 2H, J=6.4 Hz), 3.88–3.22 (m, 4H), 3.55 (s, 3H), 3.49 (s, 3H), 2.36–2.24 (m, 1H), 2.08–1.93 (m, 1H), 1 .19–1.13 (t, 3H, J=7.0 Hz), 1.11–1.06 (t, 3H, J=7.0 Hz), 0.94–0.88 (t, 3H, J=7.4 Hz) ppm; $^{13}$C (CDCl$_{13}$): 191.6, 169.0, 148.0, 145.9, 134.8, 132.4, 130.0, 129.6, 128.9, 128.6, 126.0, 92.8, 84.4, 77.2, 71.4, 58.9, 56.8, 41.5, 40.8, 28.6, 13.6, 12.3, 7.4 ppm; IR (film): 1677, 1641, 1619 cm$^{-1}$; MS (EI+): m/z 428 (M$^+$), 383, 328,100 (100%); HRMS (EI+): Calc. for C$_{24}$H$_{32}$N$_2$O$_5$: 428.2311 (M$^+$); Found: 428.2310 (M$^+$); EA:(Calc) C: 67.20 (67.27); H: 7.69 (7.53); N: 6.40 (6.54).

Example 11

A mixture of potassium tert-butoxide (523 mg, 4.44 mmol), 2-cyanoacetamide, VI (345 mg, 4.07 mmol), and methyl sulfoxide (27 ml) in a flame-dried flask was stirred at room temperature for 15 minutes prior to addition of a solution of enone XVIII (1.582 g, 3.69 mmol) in methyl sulfoxide (10 ml). The reaction mixture was stirred at room temperature for 30 minutes, then it was poured into saturated aqueous NaHCO$_3$—NaCl solution. The aqueous layer was extracted with 2:8 EtOH/CHCl$_3$, and the extracts were sequentially washed with H20 and saturated aqueous NaCl, dried (Na$_2$SO$_4$) and concentrated. Flash chromatography (0.5% MeOH/CHCl$_3$) provided the diastereomeric mixture of Michael-adducts XIX (1.892 g, 3.69 mmol, 100%).

This material was dissolved in acetic acid (38 ml) and treated with selenium (IV) oxide (56% adsorbed on silica gel; 2.1 g, 0.94 mmol) and tert-butyl hydroperoxide (1.54 ml, 70%; in H$_2$O). The mixture was heated to 110° C. for one hour, whereupon a pyridone has formed. Then 10% aqueous sulfuric acid (3.8 ml) was added and the solution was stirred at 110° C. for one additional hour. The solution was cooled to room temperature, carefully neutralized with saturated aqueous NaHCO₃—NaCl (vigorous foaming), extracted with 2:8 EtOH/CHCl₃, sequentially washed with H₂O and saturated aqueous NaCl, dried (Na₂SO₄) and concentrated to afford 1.068 g (68% from enone XVIII) of XX as a yellow foam.

[a]$_D$: −38.8° (c 1.025, CHCl₃); ¹H (CDCl₃): 8.38 (s, 1H) 8.18–8.14 (dd, 1H, J₁=8.7 Hz), 7.93–7.89 (dd,1H, J₁=8.6 Hz, J₂=0.9 Hz), 7.87–7.81 (dt, 1H, J₁=6.9 Hz, J₂=1.4 Hz), 7.71–7.65 (dt, 1H, J₁=7.0 Hz, J₂=1.2 Hz), 7.63 (s, 1H), 4.84–4.67 (AB, 2H, J=11.2 Hz), 4.00–3.91 (m, 1H), 3.64 (s, 3H), 3.61–3.45 (m, 1H), 3.38–3.17 (m, 2H), 2.51–2.39 (m, 1H), 2.23–2.08 (m, 1H), 1.30–1.25 (t, 3H, J=7.0 Hz), 1.19–1.13 (t, 3H, J=7.0 Hz), 1.00–0.94 (t, 3H, J=7.4 Hz) ppm; ¹³C (CDCl₃): 169.3, 166.4, 166.2, 157.4, 148.3, 148.2, 146.8, 140.4, 131.3, 129.5, 128.9, 128.7, 128.0, 127.5, 113.7, 104.7, 88.9, 72.3, 58.6, 42.7, 31.9, 14,8, 14.1, 7.7 ppm; IR (film): 1780, 1677, 1635 cm⁻¹; MS (EI+): m/z 449 (M⁺), 349, 317, 100 (100%); HRMS (EI+): Calc. for C₂₅H₂₇N₃O₅: 449.1951 (M⁺); Found: 449.1951 (M⁺); EA: (Calc) C: 66.99 (66.80); H: 6.52 (6.05); N: 8.95 (9.35).

Example 12

Sodium borohydride (366 mg, 9.44 mmol) was added in two portions to a cold (0° C.) solution of lactone XX (424 mg, 0.94 mmol), cerium (III) chloride (624 mg, 2.36 mmol) and EtOH (47 ml). The mixture was allowed to warm to room temperature, whereupon reduction of the lactone to the corresponding lactol occurred (20 minutes). The mixture was then heated to 45° C. for 30 minutes to effect reduction to the diol, cooled, poured into saturated aqueous NaHCO3—NaCl, extracted with 2:8 EtOH/CHCl3, dried (Na₂SO₄) and concentrated to afford diol XXI as a yellow foam, which was used without further purification.

[a]$_D$: +72.1° (c 1.200, CHCl₃); ¹H (CDCl₃): 8.31(s, 1H) 8.14–8.11 (d, 1H, J=8.4 Hz), 7.90–7.86 (dd,1H, J₁=8.2 Hz, J₂=1.0 Hz), 7.83–7.77 (dt, 1H, J₁=7.0 Hz, J₂=1.3 Hz), 7.66–7.60 (t, 1H, J=7.2 Hz), 7.51 (s, 1H), 5.44 (s, 1H), 4.78–4.60 (AB, 2H, J=11.4 Hz), 4.71 (s.2H), 4.31 (s, 1H, broad), 3.63–3.04 (m, 4H), 3.55 (s, 3H), 2.28–2.08 (m, 2H), 1.20–1.15 (t, 3H, J=7.0 Hz) 1.00–0,94 (t, 3H, J=7.3 Hz), 0-94-0.88 (t, 3H, J=7.2 Hz) ppm; ¹³C (CDCl₃): 171.8, 164.1, 151.4, 149.1, 146.8, 140.3, 140.0, 132.2, 130.9, 129.3, 128.2, 127.7, 127.5, 106.9, 77.2, 76.7, 72.6, 58.4, 42.1, 41.6, 31.3, 12.7, 12.4, 7.7 ppm; IR (film): 3330 *(broad), 1623 cm⁻¹; MS (EI+): m/z 454 (MH⁺), xx (100%); HRMS (EI+): Calc. for C₂₅H₃₁N₃O₅: 449.1951 (M+); Found: 449.1951 (M+); EA: (Calc) C: 65.64 (66.21); H: 7.32 (6.89); N: 8.43 (9.26).

Example 13

Crude diol XXI, dissolved in 19 ml 60% ethanolic sulfuric acid, was heated to 115° for 5 hours. The cooled reaction mixture was carefully added to saturated aqueous NaHCO3—NaCl (vigorous foaming), extracted with 2:8 EtOH/CHCl3, dried (Na2SO4), and concentrated. The residue was chromatographed (1% MeOH/CHCl3) to yield 309 mg (94% from lactone 10) of pure 1, identical in all respects to an authentic sample of natural 1.

What is claimed is:
1. A process for preparing camptothecin comprising the steps of:

a) providing a quantity of a first reagent of the formula:

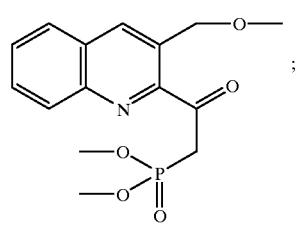

IV b) mixing IV in solution with a second reagent of the formula:

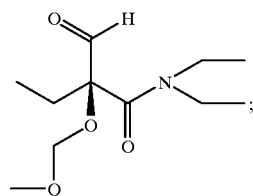

to form:

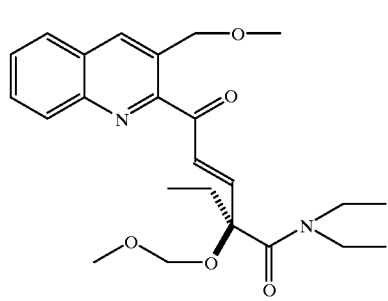

XVIII c) mixing XVIII in solution with a third reagent of the formula:

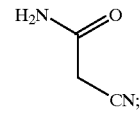

to form:

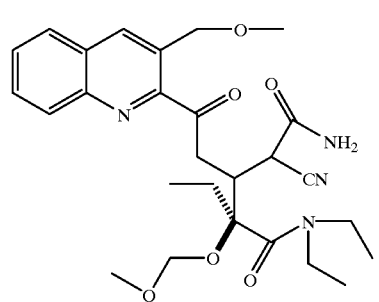

XIX d) oxidizing XIX in the presence of a dissolved hydrolyzing agent to form the intermediate:

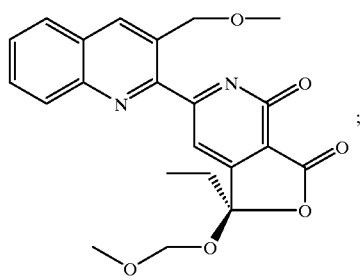
e) reducing XX in solution to form the intermediate:
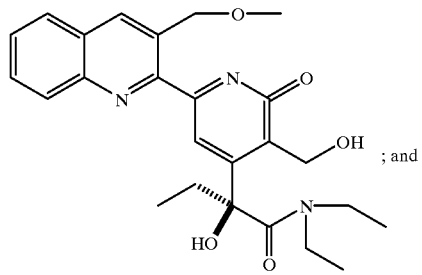
f) cyclizing XXI in an acid solution to form camptothecin.
* * * * *

UNITED STATES PATENT AND TRADEMARK OFFICE
CERTIFICATE OF CORRECTION

| | | |
|---|---|---|
| PATENT NO. | : 6,218,540 B1 | Page 1 of 1 |
| APPLICATION NO. | : 09/230683 | |
| DATED | : April 17, 2001 | |
| INVENTOR(S) | : Marco Ciufolini et al. | |

It is certified that error appears in the above-identified patent and that said Letters Patent is hereby corrected as shown below:

In Column 1, under the heading "CROSS-REFERENCE TO RELATED APPLICATIONS" and after the sentence ending on Line 10, the following sentence should be added:

"This invention was made with government support under Grant Number R 01 CA55268 awarded by the National Institutes of Health (NIH). The government has certain rights in the invention."

Signed and Sealed this
First Day of March, 2011

David J. Kappos
*Director of the United States Patent and Trademark Office*